US010000565B2

(12) United States Patent
Basson et al.

(10) Patent No.: US 10,000,565 B2
(45) Date of Patent: Jun. 19, 2018

(54) USE OF IL-1 β BINDING ANTIBODIES FOR TREATING PERIPHERAL ARTERIAL DISEASE

(71) Applicants: Craig Basson, Needham, MA (US); Mark Fishman, Newton Center, MA (US); Tom Thuren, Succasunna, NJ (US); Shi Yin Foo, Brookline, MA (US)

(72) Inventors: Craig Basson, Needham, MA (US); Mark Fishman, Newton Center, MA (US); Tom Thuren, Succasunna, NJ (US); Shi Yin Foo, Brookline, MA (US)

(73) Assignee: Novartis AG, Basel (CH)

( * ) Notice: Subject to any disclaimer, the term of this patent is extended or adjusted under 35 U.S.C. 154(b) by 0 days. days.

(21) Appl. No.: 14/442,536

(22) PCT Filed: Nov. 14, 2013

(86) PCT No.: PCT/US2013/070042
§ 371 (c)(1),
(2) Date: May 13, 2015

(87) PCT Pub. No.: WO2014/078502
PCT Pub. Date: May 22, 2014

(65) Prior Publication Data
US 2016/0326243 A1 Nov. 10, 2016

Related U.S. Application Data

(60) Provisional application No. 61/727,334, filed on Nov. 16, 2012.

(51) Int. Cl.
*C07K 16/24* (2006.01)
*A61K 39/00* (2006.01)

(52) U.S. Cl.
CPC ...... *C07K 16/245* (2013.01); *A61K 2039/505* (2013.01); *A61K 2039/545* (2013.01); *C07K 2317/21* (2013.01); *C07K 2317/56* (2013.01); *C07K 2317/565* (2013.01); *C07K 2317/76* (2013.01); *C07K 2317/92* (2013.01)

(58) Field of Classification Search
CPC .............. C07K 16/245; C07K 2317/92; C07K 2317/76; C07K 2317/565; C07K 2317/56; C07K 2317/21; A61K 2039/545; A61K 2039/505
See application file for complete search history.

(56) References Cited

FOREIGN PATENT DOCUMENTS

| WO | WO 2008/077145 A2 | 6/2008 |
|---|---|---|
| WO | 2009120307 A2 | 10/2009 |
| WO | WO 2009/149185 A2 | 12/2009 |
| WO | WO 2009/149189 A2 | 12/2009 |
| WO | WO 2010/028275 A1 | 3/2010 |
| WO | WO 2010/087972 A2 | 8/2010 |
| WO | WO 2010/138939 A1 | 12/2010 |
| WO | WO 2011/047266 A1 | 4/2011 |
| WO | WO 2012/018790 A2 | 2/2012 |
| WO | WO 2013/049278 A1 | 4/2013 |

OTHER PUBLICATIONS

Vajdos et al. Comprehensive functional maps of the antigen-binding site of an anti-ErbB2 antibody obtained with shotgun scanning mutagenesis. J. Mol. Biol. 320:415-428, 2002.*
Bendermacher et al., "Applicability of the ankle-brachial-index measurement as screening device for high cardiovascular risk: an observational study", BMC Cardiovascular Disorders, 2012, vol. 12, No. 59, pp. 1-7.
Korhonen et al., "Assessment of cardiovascular risk in primary health care", Scandinavian Journal of Primary Health Care, 2012, vol. 30, pp. 101-106.
Chen et al., "Periodontitis May Increase the Risk of Peripheral Arterial Disease", European Journal of Vascular Surgery, vol. 35, No. 2, pp. 153-158, Oct. 25, 2007.
Hensen et al., "Impact of interleukin-1[beta] antibody (canakinumab) on glycaemic indicators in patients with type 2 diabetes mellitus: Results of secondary endpoints from a randomized, placebo-controlled trial", Diabetes & Metabolism, vol. 39, No. 6, pp. 524-531, Dec. 1, 2013.
Russell et al. (2017) "Effects of Canakinumab in Patients with Peripheral Artery Disease", Abstract No. 11, presented at Arteriosclerosis, Thrombosis and Vascular Biology | Peripheral Vascular Disease Scientific , May 4-6, 2017, Minneapolis, MN.
Russell et al. (May 4, 2017) "Effects of Canakinumab in Patients with Peripheral Artery Disease", slides accompanying oral presentation delivered at Arteriosclerosis, Thrombosis and Vascular Biology | Peripheral Vascular Disease Scientific, May 4-6, 2017, Minneapolis, MN.
Ridker at al , "Interleukin-1β inhibition and the prevention of recurrent cardiovascular events,", AM Heart Journal, 2011, vol. 162, No. 4, pp. 597-605.
Gerhard-Herman et al., "2016 AHA/ACC guideline on the management of patients with lower extremity peripheral artery disease: executive summary", Circulation, 2017, vol. 135: e686-e725.
Cosentyx® Product Insert, Novartis Pharmaceuticals Corporation, dated Sep. 2017.
Taltz® Product Insert, Eli Lilly and Company, dated Mar. 2016.
Remicade® prescribing information, Janssen Biotech, Inc., dated Oct. 2017.
Wolbink et al., "Dealing with immunogenicity of biologicals: assessment and clinical relevance", Current Opinion in Rheumatology, 2009, vol. 21(3): 211-215.

(Continued)

*Primary Examiner* — Ruixiang Li
(74) *Attorney, Agent, or Firm* — Jim Lynch

(57) ABSTRACT

The present invention relates to a method for treating or alleviating the symptoms of peripheral arterial disease (PAD) in a subject, comprising administering about 25 mg to about 300 mg of an IL-1β binding antibody or functional fragment thereof.

15 Claims, No Drawings

(56) References Cited

OTHER PUBLICATIONS

Mok et al., "Drug levels, anti-drug antibodies, and clinical efficacy of the anti-TNFx biologics in rheumatic diseases", Clinical Rheumatology, 2013, vol. 32: 1429-1435.
Salvana et al., "Infectious complicaions associated with monoclonal antibodies and related small molecules", Clinical Microbiology Reviews, 2009, vol. 22(2): 274-290.

* cited by examiner

# USE OF IL-1 β BINDING ANTIBODIES FOR TREATING PERIPHERAL ARTERIAL DISEASE

TECHNICAL FIELD

The present disclosure relates to a novel use and dosage regimens of an IL-β binding antibody or functional fragments thereof, for treating or alleviating the symptoms of peripheral arterial disease.

BACKGROUND OF THE DISCLOSURE

Periferal arterial disease PAD, also known as peripheral vascular disease (PVD) or peripheral arterial occlusive disease (PAOD) refers to the obstruction of large arteries not within the coronary, aortic arch vasculature, or brain. PAD can result from atherosclerosis, inflammatory processes leading to stenosis, an embolism, or thrombus formation. It causes either acute or chronic ischemia (lack of blood supply). PAD is a form of atherosclerotic disease that affects the peripheral arteries. It commonly manifests in the blood vessels of the legs as claudication, an intermittent pain that occurs with exercise and/or at rest. PAD is prevalent in smokers and diabetics; its incidence increases with age. PAD affects ~10 million individuals in the US alone. Management of PAD overlaps with coronary disease risk modification, but approved medical therapies for PAD affect platelet viscosity to improve blood flow to peripheral muscles and do not modify disease. PAD shares pathologic features with coronary atherosclerosis, such a chronic vascular inflammation. Interleukins (ILs) are key mediators in the chronic vascular inflammatory response. IL-1β activates endothelial cells, leading to the upregulation of adhesion molecules that promote inflammatory cell adhesion to the vessel wall. IL-1β also increases extracellular matrix and collagen deposition, thereby contributing to plaque burden and arterial wall thickening. Antagonism of IL-1β is an attractive target to ameliorating vessel wall inflammation associated with atherosclerosis.

Inhibition of IL-1 activity is being currently explored for a number of cardiovascular indications via different mechanisms. Anakinra (Kineret) is a human interleukin-1 receptor antagonist that requires daily subcutaneous dosing of approximately 100 mg for efficacy. The MRC-ILA-HEART study is a clinical trial investigating the effects of anakinra upon markers of inflammation in patients with non-ST elevation myocardial infarction (NSTEMI) (Crossman, et al., 2008).

ACZ885 (canakinumab) is a high-affinity, fully human monoclonal antibody to interleukin-1β, developed originally for the treatment of IL-1β-driven inflammatory diseases. Canakinumab has been approved under the trade name ILARIS® in the US for patients ≥4 year of age with Cryopyrin-Associated Periodic Syndromes (CAPS), [Familial Cold-Associated Syndrome (FCAS) and Muckle-Wells syndrome (MWS) phenotypes included. Canakinumab has also received regulatory approvals for treatment of SJIA and gout.

SUMMARY OF THE DISCLOSURE

Accordingly, in a one aspect, the present disclosure is directed to a method for treating or alleviating the symptoms of peripheral arterial disease (PAD) in a subject, comprising administering about 25 mg to about 300 mg of an IL-1β binding antibody or functional fragment thereof. The therapy of the invention will decrease the amount of plaque in peripheral arteries, and/or may also improve endothelial function to promote more blood flow, and thereby improve the ability of patients to ambulate without pain.

Accordingly, in a another aspect, the present disclosure is directed to an IL-1β binding antibody or a functional fragment thereof for use as a medicament for treating or alleviating the symptoms of peripheral arterial disease (PAD) in a subject, comprising administering about 25 mg to about 300 mg of an IL-1β binding antibody or functional fragment thereof.

Accordingly, in yet another aspect, the present disclosure is directed to the use of an IL-1β binding antibody or a functional fragment thereof for the manufacture of a medicament for treating or alleviating the symptoms of peripheral arterial disease (PAD) in a subject, comprising administering about 25 mg to about 300 mg of an IL-1β binding antibody or functional fragment thereof.

Further features and advantages of the disclosure will become apparent from the following detailed description of the invention.

DETAILED DESCRIPTION OF THE DISCLOSURE

Periferal arterial disease PAD, also known as peripheral vascular disease (PVD) or peripheral arterial occlusive disease (PAOD) refers to the obstruction of large arteries not within the coronary, aortic arch vasculature, or brain. PAD can result from atherosclerosis, inflammatory processes leading to stenosis, an embolism, or thrombus formation. It causes either acute or chronic ischemia (lack of blood supply). Often PAD is a term used to refer to atherosclerotic blockages found in the lower extremity.

The present invention provides a method for treating or alleviating the symptoms of peripheral arterial disease (PAD) in a subject, comprising administering about 25 mg to about 300 mg of an IL-1β binding antibody or functional fragment thereof. In one embodiment of any method of the invention, the subject has moderate PAD. Moderate PAD is associated with an ankle-brachial index (ABI) below 0.8. ABI or ABPI (ankle brachial pressure index) is determined by comparing the blood pressure measured in the ankles to the blood pressure measured in the arms. Patients with severe ichemic disease and severe PAD has an ABI below 0.5 or below 0.4 and these patients can also benefit from treatment with the methods and uses according to the present invention. In one embodiment the subject is exhibiting an ankle-brachial index between 0.5 and 0.85 in at least one leg before treatment. In another embodiment, the subject is exhibiting an ankle-brachial index less than 0.5 in at least one leg or the subject is exhibiting an ankle-brachial index less than 0.9 in at least one leg.

Moderate PAD is associated with the subject having symptomatic intermittent claudication, i.e., the patients exhibiting severe pain when walking relatively short distances e.g., less than 150 m or less than 400 m.

In one embodiment of any method of the invention, the subject has improved vascular structure and function after 3 months of treatment or after 12 months of treatment. In one embodiment, reduced plaque burden in the peripheral artery walls of said subject is observed after at least 3 months of treatment or at least 12 months of treatment. The reduced plaque burden compared to before treatment in said subject can be determined in the superficial femoral artery after at least 3 months of treatment or after at least 12 months of treatment. The improvements of vascular structure and function can be determined by magnetic resonance imaging (MRI).

The subject's ability to walk for 6 min will improve after treatment with the methods and uses according to the present invention.

IL-1β binding antibody or functional fragment thereof is administered every 2 weeks, twice a month, monthly, every 6 weeks, every 2 months, every 3 months, every 4 months, every 5 months, or every 6 months from the first administration. In one embodiment, said IL-1β binding antibody or functional fragment thereof is administered monthly.

In one embodiment, said method comprises administering about 25, 50, 75, 80, 100, 125, 150, 175, 200, 225, 250, 275, 300 mg or any combination thereof of the IL-1β binding antibody or functional fragment thereof. Said method comprises administering about 50 mg, about 80 mg or about 200 mg or about 300 mg of the IL-1β binding antibody or functional fragment thereof. In one embodiment, said method comprises administering about 150 mg of the IL-1β binding antibody or functional fragment thereof.

In another embodiment said method comprising administering the patient an additional dose of about 25 mg to about 300 mg of the IL-1β binding antibody or functional fragment thereof at week 2, week 4 or week 6 from the first administration.

In one embodiment of any method of the invention, said IL-1β binding antibody or functional fragment thereof is an IL-1β binding antibody. In one embodiment of any method of the invention, said IL-1β binding antibody or functional fragment thereof is capable of inhibiting the binding of IL-1β to its receptor and has a $K_D$ for binding to IL-1β of about 50 pM or less.

In other embodiments of any method of the invention said IL-1β binding antibody is selected from the group consisting of:
  a) an IL-1β binding antibody directed to an antigenic epitope of human IL-1β which includes the loop comprising the Glu64 residue of the mature IL-1β, wherein said IL-1β binding antibody is capable of inhibiting the binding of IL-1β to its receptor, and further wherein said IL-1β binding antibody has a $K_D$ for binding to IL-1β of about 50 pM or less;
  b) an IL-1β binding antibody that competes with the binding of an IL-1β binding antibody comprising a VH domain comprising SEQ ID NO:1 and a VL domain comprising SEQ ID NO:2;
  c) an IL-1β binding antibody comprising the three CDRs of SEQ ID NO:3, SEQ ID NO:4, SEQ ID NO:5;
  d) an anti-IL-1β binding antibody comprising the three CDRs of SEQ ID NO:6, SEQ ID NO:7, SEQ ID NO:8;
  e) an anti-IL-1β binding antibody comprising the three CDRs of SEQ ID NO:3, SEQ ID NO:4, SEQ ID NO:5 and the three CDRs of SEQ ID NO:6, SEQ ID NO:7, SEQ ID NO:8;
  f) an anti-IL-1β binding antibody comprising a VH domain comprising SEQ ID NO:1;
  g) an anti-IL-1β binding antibody comprising a VL domain comprising SEQ ID NO:2;
  h) an anti-IL-1β binding antibody comprising a VH domain comprising SEQ ID NO:1 and a VL domain comprising SEQ ID NO:2.

In one embodiment of any method of the invention, said IL-1β binding antibody or fragment thereof comprises the 3 CDRs of SEQ ID NO:1 are set forth in SEQ ID NO:3, 4, and 5 and wherein the 3 CDRs of SEQ ID NO:2 are set forth in SEQ ID NO:6, 7, and 8.

In other embodiments of any method of the invention, the IL-1β binding antibody comprises:
  a) a VH having a first CDR having 0, 1 or 2 amino acid substitutions in comparison to the CDR set forth in SEQ ID NO:3, a second CDR having 0, 1 or 2 amino acid substitutions in comparison to the CDR set forth in SEQ ID NO:3, a third CDR having 0, 1 or 2 amino acid substitutions in comparison to the CDR set forth in SEQ ID NO:5; and
  b) a VL having a first CDR having 0, 1 or 2 amino acid substitutions in comparison to the CDR set forth in SEQ ID NO:6, a second CDR having 0, 1 or 2 amino acid substitutions in comparison to the CDR set forth in SEQ ID NO:7, and a third CDR having 0, 1 or 2 amino acid substitutions in comparison to the CDR set forth in SEQ ID NO:8, wherein said antibody has a $K_D$ for IL-1beta of 50 pM or less and wherein said antibody inhibits the binding of IL-1β to its receptor.

Substituted amino acids are ideally conservative substitutions, and once substituted a skilled artisan could use an assay such as those described in WO02/16436.

In some embodiments of any of the method described above, the antibody or fragment binds to human IL-1β with a dissociation constant of about 50 pM or less. In some embodiments, the antibody or fragment binds to human IL-Iβ with a dissociation constant of about 500 pM or less. In some embodiments, the IL-1β binding antibody or functional fragment thereof binds to human IL-Iβ with a dissociation constant of about 250 pM or less. In some embodiments, the IL-13 binding antibody or functional fragment thereof binds to human IL-1β with a dissociation constant of about 100 pM or less. In some embodiments of any of the methods described above, the IL-1β binding antibody or functional fragment thereof binds to human IL-1β with a dissociation constant of about 5 pM or less. In some embodiments, the IL-1β binding antibody or functional fragment thereof binds to human IL-1β with a dissociation constant of about 1 pM or less. In some embodiments, the IL-1β binding antibody or functional fragment thereof binds to human IL-1β with dissociation constant of about 0.3 pM or less.

In some embodiments of any and/or all of the methods described above, the IL-1β binding antibody or functional fragment thereof is a neutralizing antibody.

One example of an IL-1β binding antibody is canakinumab which has a heavy chain variable region (VH) is set forth as SEQ ID NO:1 of the sequence listing. CDR1 of the VH of canakinumab is set forth as SEQ ID NO:3 of the sequence listing. CDR2 of the VH of canakinumab is set forth as SEQ ID NO:4 of the sequence listing. CDR3 of the VH of canakinumab is set forth as SEQ ID NO:5 of the sequence listing.

The canakinumab light chain variable region (VL) is set forth as SEQ ID NO:2 of the sequence listing. CDR1 of the VL of canakinumab is set forth as SEQ ID NO:6 of the sequence listing. CDR2 of the VL of canakinumab is set forth as SEQ ID NO:7 of the sequence listing. CDR3 of the VL of canakinumab is set forth as SEQ ID NO:8 of the sequence listing.

In some embodiments of any and/or all of the methods described above, the anti-IL-1β binding antibody or binding fragment thereof competes with the binding of an antibody having the light chain variable region of SEQ ID NO:1 and the heavy chain variable region of SEQ ID NO:2.

In some embodiments, the disclosed methods comprise administering an anti-IL-1β binding antibody having the three CDRs of SEQ ID NO:1. In further embodiments, the three CDRs of SEQ ID NO:1 are set forth as SEQ ID NOs:3-5. In some embodiments, the disclosed methods comprise administering an anti-IL-1β binding antibody having the three CDRs of SEQ ID NO:2. In further embodiments, the three CDRs of SEQ ID NO:2 are set forth as SEQ ID NOs:6-8.

Preferably the IL-1β binding antibody is canakinumab. Canakinumab is a fully human monoclonal anti-human IL-1β antibody of the IgG1/k isotype, being developed for the treatment of IL-1β driven inflammatory diseases. It is designed to bind to human IL-1β and thus blocks the interaction of this cytokine with its receptors. The antagonism of the IL-1β mediated inflammation using canakinumab in lowering high sensitivity C-reactive protein (hsCRP) and other inflammatory marker levels has shown an acute phase response in patients with Cryopyrin-Associated Periodic Syndrome (CAPS) and rheumatoid arthritis. This evidence has been replicated in patients with type 2 diabetes mellitus (T2DM) using canakinumab and with other IL-1β antibody therapies in development.

Canakinumab is disclosed in WO02/16436 which is hereby incorporated by reference in its entirety.

In other embodiments of any method of the invention, said IL-1β binding antibody or functional fragment thereof is selected from the group consisting of gevokizumab, LY-2189102 or AMG-108.

Said IL-1β binding antibody or functional fragment thereof is administered parentally, e.g., intravenously or subcutaneously. Preferably, canakinumab is administered subcutaneously. Canakinumab can be administered in a reconstituted formulation comprising canakinumab at a concentration of 10-200 mg/ml, 270 mM sucrose, 30 mM histidine and 0.06% polysorbate 80, wherein the pH of the formulation is 6.5. Canakinumab can also be administered in a liquid formulation comprising canakinumab at a concentration of 10-200 mg/ml, mannitol, histidine and polysorbate 80, wherein the pH of the formulation is 5.5-7.0. Canakinumab can also be administered in a liquid formulation comprising canakinumab at concentration: 10-200 mg/ml, 270 mM mannitol, 20 mM histidine and 0.04% polysorbate 80, wherein the pH of the formulation is 6.5.

Said IL-1β binding antibody e.g. canakinumab or functional fragment can be administered to the patient in a liquid form or lyophilized form for reconstitution contained in a prefilled syringe. In one embodiment, the prefilled syringe is contained in an autoinjector.

In other embodiments of any method of the invention, said patient is concomitantly receiving a statin such as lovastatin, pravastatin, simvastatin, fluvastatin, atorvastatin, cerivastatin, mevastatin, pitavastatin, rosuvastatin Preferably said patient is concomitantly receiving simvastatin, atorvastatin, rosuvastatin or aspirin. In one aspect, said patient is concomitantly receiving cilostazol or pentoxyfylline. In other aspects, said patient is concomitantly receiving beta-adrenergic blocking drugs such as esmolol, metoprolol, nadolol, penbutolol; or an angiotensin-converting enzyme (ACE) inhibitor such as ramipril, ramiprilat, captopril, lisinopril; or an angiotensin II receptor blocker such as losartan, valsartan, olmesartan, irbesartan, candesartan, telmisartan, eprosartan; or an inhibitor of platelet aggregation such clopidogrel, elinogrel, prasugrel, cangrelor, ticagrelor, ticlopidine, dipyridamole, picopamide eptifibatide, abciximab, eptifibatide, tirofiban or terutroban; or a nitrate such as glyceryl trinitrate (GTN)/nitroglycerin, isosorbide dinitrate, isosorbide mononitrate.

According to another aspect of the invention, an IL-1β binding antibody or a functional fragment thereof for use as a medicament for treating or alleviating the symptoms of peripheral arterial disease (PAD) in a subject, comprising administering about 25 mg to about 300 mg of an IL-1β binding antibody or functional fragment thereof.

According yet another aspect of the invention, the use of an IL-1β binding antibody or a functional fragment thereof is provided for the manufacture of a medicament for treating or alleviating the symptoms of peripheral arterial disease (PAD) in a subject, comprising administering about 25 mg to about 300 mg of an IL-1β binding antibody or functional fragment thereof.

In the following, various aspects of the two uses stated in the two paragraphs above are described and all these aspects could be combined together. The skilled person realizes that the teaching in the following six pages are all combinable with each other and particular aspect combining features from various parts of these pages will be considered to be adequately disclosed to the skilled person. In addition, all embodiment combining all the various aspects below with selecting canakinumab as IL-1β binding antibody or a functional fragment containing the same variable domain as canakinumab will be regarded as especially preferred.

In one aspect the subject has moderate PAD. Moderate PAD is associated with an ankle-brachial index (ABI) below 0.8. Patients with severe ichemic disease and severe PAD has an ABI below 0.5 or below 0.4 and these patients can also benefit from treatment with the methods and uses according to the present invention. In one embodiment the subject is exhibiting an ankle-brachial index between 0.5 and 0.85 in at least one leg before treatment. In another embodiment, the subject is exhibiting an ankle-brachial index less than 0.5 in at least one leg or the subject is exhibiting an ankle-brachial index less than 0.9 in at least one leg.

Moderate PAD is associated with the subject having symptomatic intermittent claudication, i.e., the patients exhibiting severe pain when walking relatively short distances like some 100 m e.g., less than 150 m or less than 400 m.

In one embodiment of any use of the invention, the subject has improved vascular structure and function after 3 months of treatment or after 12 months of treatment. In one embodiment, reduced plaque burden in the peripheral artery walls of said subject is observed after at least 3 months of treatment or at least 12 months of treatment. The reduced plaque burden compared to before treatment in said subject can be determined in the superficial femoral artery after at least 3 months of treatment or after at least 12 months of treatment. The improvements of vascular structure and function can be determined by magnetic resonance imaging (MRI).

The subject's ability to walk for 6 min will improve after treatment with the methods and uses according to the present invention.

IL-1β binding antibody or functional fragment thereof is administered every 2 weeks, twice a month, monthly, every 6 weeks, every 2 months, every 3 months, every 4 months, every 5 months, or every 6 months from the first administration. In one embodiment, said IL-1β binding antibody or functional fragment thereof is administered monthly.

In other embodiments of the uses described above, said patient is to be administered about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 mg or any combination thereof of said IL-1β binding antibody or functional fragment thereof.

In one embodiment, the use comprises administering about 25, 50, 75, 80, 100, 125, 150, 175, 200, 225, 250, 275, 300 mg or any combination thereof of the IL-1β binding antibody or functional fragment thereof. The use comprises administering about 50 mg, about 80 mg or about 200 mg or about 300 mg of the IL-1β binding antibody or functional fragment thereof.

In one embodiment, the use comprises administering about 150 mg of the IL-1β binding antibody or functional fragment thereof.

In another embodiment the use comprising administering the patient an additional dose of about 25 mg to about 300 mg of the IL-1β binding antibody or functional fragment thereof at week 2, week 4 or week 6 from the first administration.

In one embodiment of any use of the invention, said IL-1β binding antibody or functional fragment thereof is an IL-1β binding antibody. In one embodiment of any use of the invention, said IL-1β binding antibody or functional fragment thereof is capable of inhibiting the binding of IL-1β to its receptor and has a $K_D$ for binding to IL-1β of about 50 pM or less.

In other embodiments of any use of the invention said IL-1β binding antibody is selected from the group consisting of:
a) an IL-1β binding antibody directed ton antigenic epitope of human IL-1β which includes the loop comprising the Glu64 residue of the mature IL-1β, wherein said IL-1β binding antibody is capable of inhibiting the binding of IL-1β to its receptor, and further wherein said IL-1β binding antibody has a $K_D$ for binding to IL-1β of about 50 pM or less;
b) an IL-1β binding antibody that competes with the binding of an IL-1β binding antibody comprising a VH domain comprising SEQ ID NO:1 and a VL domain comprising SEQ ID NO:2;
c) an anti-IL-1β binding antibody comprising the three CDRs of SEQ ID NO:3, SEQ ID NO:4, SEQ ID NO:5;
d) an anti-IL-1β binding antibody comprising the three CDRs of SEQ ID NO:6, SEQ ID NO:7, SEQ ID NO:8;
e) an anti-IL-1β binding antibody comprising the three CDRs of SEQ ID NO:3, SEQ ID NO:4, SEQ ID NO:5 and the three CDRs of SEQ ID NO:6, SEQ ID NO:7, SEQ ID NO:8;
f) an anti-IL-1β binding antibody comprising a VH domain comprising SEQ ID NO:1;
g) an anti-IL-1β binding antibody comprising a VL domain comprising SEQ ID NO:2;
h) an anti-IL-1β binding antibody comprising a VH domain comprising SEQ ID NO:1 and a VL domain comprising SEQ ID NO:2.

In one embodiment of any use of the invention, said IL-1β binding antibody or fragment thereof comprises the 3 CDRs of SEQ ID NO:1 are set forth in SEQ ID NO:3, 4, and 5 and comprises the 3 CDRs of SEQ ID NO:2 are set forth in SEQ ID NO:6, 7, and 8.

In other embodiments of any use of the invention, said IL-1β binding antibody or functional fragment thereof comprises:
a) a VH having a first CDR having 0, 1 or 2 amino acid substitutions in comparison to the CDR set forth in SEQ ID NO:3, a second CDR having 0, 1 or 2 amino acid substitutions in comparison to the CDR set forth in SEQ ID NO:3, a third CDR having 0, 1 or 2 amino acid substitutions in comparison to the CDR set forth in SEQ ID NO:5; and
b) a VL having a first CDR having 0, 1 or 2 amino acid substitutions in comparison to the CDR set forth in SEQ ID NO:6, a second CDR having 0, 1 or 2 amino acid substitutions in comparison to the CDR set forth in SEQ ID NO:7, and a third CDR having 0, 1 or 2 amino acid substitutions in comparison to the CDR set forth in SEQ ID NO:8; wherein said antibody has a $K_D$ for IL-1beta of 50 pM or less and wherein said antibody inhibits the binding of IL-1β to its receptor.

Substituted amino acids are ideally conservative substitutions, and once substituted a skilled artisan could use an assay such as those described in WO02/16436.

In one embodiment of any use of the invention, said IL-1β binding antibody is canakinumab. In other embodiments of any use of the invention, said IL-1β binding antibody or functional fragment thereof is selected from the group consisting of gevokizumab, LY-2189102 or AMG-108.

In some embodiments of any of the use described above, said IL-1β binding antibody or functional fragment thereof binds to human IL-1β with a dissociation constant of about 50 pM or less. In some embodiments, the antibody or fragment binds to human IL-Iβ with a dissociation constant of about 500 pM or less. In some embodiments, the IL-β binding antibody or functional fragment thereof binds to human IL-Iβ with a dissociation constant of about 250 pM or less. In some embodiments, the IL-1β binding antibody or functional fragment thereof binds to human IL-1β with a dissociation constant of about 100 pM or less. In some embodiments of any of the uses described above, the IL-13 binding antibody or functional fragment thereof binds to human IL-1β with a dissociation constant of about 5 pM or less. In some embodiments, the IL-1β binding antibody or functional fragment thereof binds to human IL-1β with a dissociation constant of about 1 pM or less. In some embodiments, the IL-1ρ binding antibody or functional fragment thereof binds to human IL-1ρ with dissociation constant of about 0.3 pM or less.

In some embodiments of any of the uses described above, the IL-1β binding antibody or fragment thereof is a neutralizing antibody.

In one aspect the IL-1β binding antibody, the canakinumab heavy chain variable region (VH) is set forth as SEQ ID NO:1 of the sequence listing. CDR1 of the VH of canakinumab is set forth as SEQ ID NO:3 of the sequence listing. CDR2 of the VH of canakinumab is set forth as SEQ ID NO:4 of the sequence listing. CDR3 of the VH of canakinumab is set forth as SEQ ID NO:5 of the sequence listing.

The canakinumab light chain variable region (VL) is set forth as SEQ ID NO:2 of the sequence listing. CDR1 of the VL of canakinumab is set forth as SEQ ID NO:6 of the sequence listing. CDR2 of the VL of canakinumab is set forth as SEQ ID NO:7 of the sequence listing. CDR3 of the VL of canakinumab is set forth as SEQ ID NO:8 of the sequence listing.

In some embodiments of any of the uses described above, the IL-1β binding antibody or fragment thereof competes with the binding of an antibody having the light chain variable region of SEQ ID NO:1 and the heavy chain variable region of SEQ ID NO:2.

In some embodiments, the disclosed uses, said IL-1β binding antibody having the three CDRs of SEQ ID NO:1. In further embodiments, the three CDRs of SEQ ID NO:1 are set forth as SEQ ID NOs:3-5. In some embodiments, the disclosed uses comprise administering an anti-IL-1β binding antibody having the three CDRs of SEQ ID NO:2. In further embodiments, the three CDRs of SEQ ID NO:2 are set forth as SEQ ID NOs:6-8.

In some embodiments, the disclosed uses comprise administering an anti-IL-1β binding antibody having the three CDRs of SEQ ID NO:1 and the three CDRs of SEQ ID NO:2. In further embodiments, the three CDRs of SEQ ID NO:1 are set forth as SEQ ID NOs:3-5 and the three CDRs of SEQ ID NO:2 are set forth as SEQ ID NOs:6-8.

In some embodiments of any of the use described above, said IL-1β binding antibody or functional fragment thereof is to be administered subcutaneously or intravenously.

When administered subcutaneously, canakinumab can be administered in a reconstituted formulation from a lyophilisate comprising canakinumab at a concentration of 10-150 mg/ml, 270 mM sucrose, 30 mM histidine and 0.06% polysorbate 80, wherein the pH of the formulation is 6.3-6.7, preferably 6.5.

When administered subcutaneously, canakinumab can be administered in a liquid formulation comprising canakinumab at a concentration of 10-200 mg/ml, mannitol, histidine and polysorbate 80 (or polysorbate 20), wherein the pH of the formulation is 5.5-7.0, or more preferred 6.3-6.7, and preferably 6.5. In one aspect the formulation comprises 10-150 mg/ml, 270 mM mannitol, 20 mM histidine and 0.04% polysorbate 80 (or polysorbate 20), wherein the pH of the formulation is 6.3-6.7, preferably 6.5.

When administered subcutaneously, canakinumab or any of said IL-1β binding antibody or functional fragment thereof can be administered to the patient in a liquid form or lyophilized form for reconstitution contained in a prefilled syringe. In one embodiment said prefilled syringe can be contained in an autoinjector. Such autoinjector makes it possible for the patient to selfadminister the liquid formulation subcutaneously in an easy manner.

In other embodiments of any use according to the invention, said patient is concomitantly receiving a statin such as lovastatin, pravastatin, simvastatin, fluvastatin, atorvastatin, cerivastatin, mevastatin, pitavastatin, rosuvastatin Preferably said patient is concomitantly receiving simvastatin, atorvastatin, rosuvastatin or aspirin. In one aspect, said patient is concomitantly receiving cilostazol or pentoxyfylline. In other aspects, said patient is concomitantly receiving beta-adrenergic blocking drugs such as esmolol, metoprolol, nadolol, penbutolol; or an angiotensin-converting enzyme (ACE) inhibitor such as ramipril, ramiprilat, captopril, lisinopril; or an angiotensin II receptor blocker such as losartan, valsartan, olmesartan, irbesartan, candesartan, telmisartan, eprosartan; or an inhibitor of platelet aggregation such clopidogrel, elinogrel, prasugrel, cangrelor, ticagrelor, ticlopidine, dipyridamole, picotamide eptifibatide, abciximab, eptifibatide, tirofiban or terutroban; or a nitrate such as glyceryl trinitrate (GTN)/nitroglycerin, isosorbide dinitrate, isosorbide mononitrate.

In another aspect the present invention provides a pharmaceutical composition comprising 25 mg/ml to about 300 mg/ml of an IL-1β binding antibody or functional fragment thereof for use as a medicament for treating or alleviating the symptoms of peripheral arterial disease (PAD) in a subject. In some aspects, said composition comprise about 25, 50, 75, 80, 100, 125, 150, 175, 200, 225, 250, 275, 300 mg/ml of the IL-1β binding antibody or functional fragment thereof.

Said composition comprise about 50 mg/ml, about 80 mg/ml, about 200 mg/ml or about 300 mg/ml of the IL-1β binding antibody or functional fragment thereof. Preferably, said composition comprises about 50 or 150 mg/ml of the IL-1β binding antibody or functional fragment thereof. Preferably, said IL-1β binding antibody is canakinumab. In one aspect said composition is a reconstituted formulation comprising 10-200 mg/ml canakinumab, 270 mM sucrose, 30 mM histidine and 0.06% polysorbate 80, wherein the pH of the formulation is 6.5. In another aspect said composition is a liquid formulation comprising 10-200 mg/ml canakinumab, mannitol, histidine and polysorbate 80, wherein the pH of the formulation is between 6.1-6.9, or 6.3-6.7. In another aspect said composition is a liquid formulation comprising 10-200 mg/ml canakinumab, 270 mM mannitol, 20 mM histidine and 0.04% polysorbate 80, wherein the pH of the formulation is 6.5.

General:

All patents, published patent applications, publications, references and other material referred to herein are incorporated by reference herein in their entirety.

As used herein, the term "comprising" encompasses "including" as well as "consisting," e.g. a composition "comprising" X may consist exclusively of X or may include something additional, e.g., X+Y.

As used herein, the term "administering" in relation to a compound, e.g., an IL-1β binding antibody or standard of care agent, is used to refer to delivery of that compound by any route of delivery.

As used herein, the term "assaying" is used to refer to the act of detecting, identifying, screening, or determining, which act may be performed by any conventional means. For example, a sample may be assayed for the presence of a particular marker by using an ELISA assay, a Northern blot, imaging, etc. to detect whether that marker is present in the sample.

As used herein, The term "about" in relation to a numerical value x means, for example, +/−10%.

As used herein, The word "substantially" does not exclude "completely," e.g., a composition which is "substantially free" from Y may be completely free from Y. Where necessary, the word "substantially" may be omitted from the definition of the disclosure.

As used herein, "C-reactive protein" and "CRP" refers to serum C-reactive protein, which is used as an indicator of the acute phase response to inflammation. The level of CRP in plasma may be given in any concentration, e.g., mg/dl, mg/L, nmol/L. Levels of CRP may be measured by a variety of well known methods, e.g., radial immunodiffusion, electroimmunoassay, immunoturbidimetry, ELISA, turbidimetric methods, fluorescence polarization immunoassay, and laser nephelometry. Testing for CRP may employ a standard CRP test or a high sensitivity CRP (hsCRP) test (i.e., a high sensitivity test that is capable of measuring low levels of CRP in a sample using laser nephelometry). Kits for detecting levels of CRP may be purchased from various companies, e.g., Calbiotech, Inc, Cayman Chemical, Roche Diagnostics Corporation, Abazyme, DADE Behring, Abnova Corporation, Aniara Corporation, Bio-Quant Inc., Siemens Healthcare Diagnostics, etc.

As used herein, the term "hsCRP" refers to the level of CRP in the blood as measured by high sensitivity CRP testing.

Each local laboratory will employ a cutoff value for abnormal (high) CRP based on that laboratory's rule for calculating normal maximum CRP. A physician generally orders a CRP test from a local laboratory, and the local laboratory reports normal or abnormal (low or high) CRP using the rule that particular laboratory employs to calculate normal CRP.

By "IL-1β binding antibody" is meant any antibody capable of binding to the IL-1β antigen either alone or associated with other molecules. The binding reaction may be shown by standard methods (qualitative assays) including, for example, a bioassay for determining the inhibition of IL-1β binding to its receptor or any kind of binding assays, with reference to a negative control test in which an antibody of unrelated specificity but of the same isotype, e.g. an anti-CD25 antibody, is used. Advantageously, the binding of the IL-1β binding antibodies used in the methods of the invention to IL-1β may be shown in a competitive binding assay.

As used herein the term "antibody" as referred to herein includes whole antibodies and any antigen binding fragment or single chains thereof (i.e., "functional fragment"). A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

As used herein, the term "functional fragment" of an antibody as used herein, refers to portions or fragments of an antibody that retain the ability to specifically bind to an antigen (e.g., IL-1β). It has been shown that the antigen-binding function of an antibody can be performed by fragments of a full-length antibody. Examples of binding fragments encompassed within the term "functional fragment" of an antibody include a Fab fragment, a monovalent fragment consisting of the $V_L$, $V_H$, CL and CH1 domains; a F(ab)2 fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989), which consists of a $V_H$ domain; and an isolated complementarity determining region (CDR). Exemplary antigen binding sites include the CDRs of canakinumab as set forth in SEQ ID NOs: 3-5 and SEQ ID NOs: 6-8. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., 1988; and Huston et al., 1988). Such single chain antibodies are also intended to be encompassed within the term "functional fragments" of an antibody. These antibody fragments are obtained using conventional techniques known to those of skill in the art, and the fragments are screened for utility in the same manner as are intact antibodies.

As used herein, the terms "monoclonal antibody" or "monoclonal antibody composition" as used herein refer to a preparation of antibody molecules of single molecular composition. A monoclonal antibody composition displays a single binding specificity and affinity for a particular epitope.

As used herein, the term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis as described in Knappik, et al. A "human antibody" need not be produced by a human, human tissue or human cell. The human antibodies of the disclosure may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

As used herein, the term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, the term "patient" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

As used herein, an antibody that "inhibits" one or more of these IL-1β functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits IL-1β activity affects a statistically significant decrease, e.g., by at least 10% of the measured parameter, by at least 50%, 80% or 90%, and in certain embodiments an antibody of the disclosure may inhibit greater than 95%, 98% or 99% of IL-17 functional activity.

As used herein the term "polypeptide", if not otherwise specified herein, includes any peptide or protein comprising amino acids joined to each other by peptide bonds, having an amino acid sequence starting at the N-terminal extremity and ending at the C-terminal extremity.

Example 1

A Multicenter, Randomized, Double-Blind, Placebo-Controlled Study of the Safety, Tolerability and Effects on Arterial Structure and Function of ACZ885 in Patients with Intermittent Claudication Because ACZ885 (canakinumab) does not cross-react with rodent, canine or pig IL-1β, preclinical efficacy data with this antibody in other species have not been obtained. However, supportive data is available from reports of reduced atherosclerosis in IL-1 knockout or IL-1 type I receptor knockout mice (Kirii, et al., 2003). IL-1 receptor antagonist deficient mice are more prone to neointima development after endothelia injury and more prone to atherogenesis (Isoda et al, m 2003; Isoda and Ohsuzu, 2006). Independent of atherosclerosis, the effects of IL-1β blockade on infarct size after coronary ligation or ischemia-reperfusion has been assessed in IL-1R1 knockout mice, and in mice treated with anakinra or IL-1β antibodies. In these studies, the blockade of IL-1 signaling is either protective or neutral (Abbate et al 2008; Salloum et al 2009). A single report (Hwang et al 2001) showed that co-administration of an anti-IL-1β antibody in an infarction model in C57BL/6 mice worsened mortality and increased rupture of the ventricular wall, but was complicated by a higher-than-normal 24-hour perioperative mortality rate in the control groups. Mice have limited collateral coronary circulations and the extent of these collateral vessels are strain-dependent. Thus these in vivo studies may have limited ability to reflect the complex multifactorial interactions that modulate IL-1β responses in humans.

In this study, subjects will be selected to be at least 3 months from previous events requiring healing processes, e.g. myocardial infarction, coronary artery bypass grafting, stroke, or carotid endarterectomy, to allow for adequate wound healing.

The objectives of this study are:
To assess the effect of ACZ885 on peripheral artery total plaque burden using MRI techniques at baseline, 3 months and 12 months.
To assess the effect of ACZ885 on serum amyloid A protein, high-sensitivity C-reactive protein and Interleukin-6 levels
To assess the effect of ACZ885 on functional capacity parameters, as measured by a 6 minute walk test, including pain-free walk distance and maximum walk distance.
To explore the effects of ACZ885 on functional capacity, as measured by outpatient activity levels (average number of steps taken daily and average time upright daily) documented by the activPAL device)

The ActivPAL™ monitor (PAL Technologies Ltd., Glasgow, UK) will be used. This device's accuracy is well documented, it provides more detailed information than some other monitors, and this has been used in other cancer studies (Maddocks et al 2011). The device is a small and lightweight (20×30×5 mm, 20 g) uniaxial accelerometer that is applied to the anterior thigh using adhesive PALStickies™ and a layer of Tegaderm™ dressing. The ActivPAL™ records periods spent sitting, standing and walking, sit-to-stand transitions, step count and rate of stepping (cadence) over a maximum period of 10 days with a fully charged new battery.

Accompanying software allows each of these outcomes to be displayed by hour, day or week. During the study the device will be worn for 6 consecutive days. These devices may be removed at night or kept on but should be removed during bathing, showering, or swimming.

The monitor also provides an estimate of energy expenditure in metabolic equivalent hours (METh), based on the time spent sitting, standing, walking and cadence; however, this outcome has not been validated.
To explore the effects of ACZ885 on serum D-dimer levels and in an ex vivo cholesterol efflux in vitro assay
To explore the effects of ACZ885 on the incidence of adjudicated major cardiovascular events and on peripheral arterial events This is a non-confirmatory, double-blind, randomized, placebo-controlled, parallel group study in patients with intermittent claudication. The study will consist of a 28 day screening period, a 28 day run-in period with initiation of a standardized exercise regimen, a 12 month treatment period and a 1 month follow-up period. MRI of the peripheral vessels will be obtained at the end of the run-in period (considered 'baseline'), and after 3 and 12 months of treatment. Additional assessments will include functional tests (6 minute walk test) and other objective measures of functional capacity (ActivPAL recorded outpatient activity) after 1, 2, 3, 6, 9 and 12 months of treatment. This design will allow for the assessment of both potential acute and chronic effects of ACZ885 on peripheral artery disease in these patients, as well as allow for an expeditious assessment of any safety concerns. Patients who meet the eligibility criteria at screening will be admitted to baseline evaluations. All baseline safety evaluation results must be available prior to dosing. Patients will attend the study site the day before dosing in each period for baseline evaluations. Following a single dose of ACZ885, pharmacokinetic, pharmacodynamic, and safety assessments will be done. Patients will then undergo Study Completion evaluations approximately 30 days after their last dose. Safety assessments will include physical examinations, ECGs, vital signs, standard clinical laboratory evaluations (hematology, blood chemistry, urinalysis) adverse event and serious adverse event monitoring.

Subjects who meet the inclusion/exclusion criteria at screening will be admitted to baseline evaluations. All baseline safety evaluation results must be available prior to dosing.

Subjects will attend the study site the day before dosing in each period for baseline evaluations. Following a single dose of ACZ885, pharmacokinetic, pharmacodynamic, and safety assessments will be made during monthly visits over 12 months. Subjects will then undergo Study Completion evaluations approx 30 days after their last dose.

Safety assessments will include physical examinations, ECGs, vital signs, standard clinical laboratory evaluations (hematology, blood chemistry, urinalysis) adverse event and serious adverse event monitoring.

This study is a randomized, placebo-controlled, double-blind study. The design of this study addresses the primary objective of evaluating the change in vascular structure and functional capacity in patients with peripheral artery disease and intermittent claudication as a result of treatment with ACZ885. Patients with an ankle-brachial index of between 0.50 and 0.85 (inclusive) will be enrolled as ABI is a predictive measure of impaired vascular blood flow to the lower extremities. Within this population, patients will additionally selected, who have a 6 minute walk distance of ≤400 m (based published data in subjects with measurable plaque volume via MRI having walk distances below 400 m (McDermott 2011)). Some measures of peripheral artery disease severity (e.g. walk distances) can be influenced by psychosocial cues such as verbal encouragement or perception of pain, or the knowledge of drug administration. Therefore this study is double-blinded to mitigate these effects. Enrollment in studies is also known to positively impact patients' motivation to exercise, which in turn improves walk distance. Therefore to minimize variability from being enrolled in the study, all patients will be enrolled in a standardized home exercise program beginning in the one month run-in period, and lasting through the duration of treatment.

As there are no currently approved or effective therapies known to mediate disease progression in PAD, placebo will be used to aim in demonstrating an effect of ACZ885 on PAD. Patients will be maintained on their stable regimen, including aspirin and statin, as recommended for PAD risk modification.

Approximately 180 subjects will be enrolled to participate in the study and randomized, with a goal of at least 120 patients expected to complete the study.

Subjects eligible for inclusion in this study have to fulfill all of the following criteria:
1. Male and female subjects age 18 to 74 years of age (inclusive) at screening, with clinical evidence of moderate peripheral artery disease. This must be demonstrated by an ankle-brachial index of 0.5-0.8 (inclusive) in at least one leg.
2. Moderate symptomatic intermittent claudication, as defined by pain and/or fatigue in any of the leg muscles with ambulation of less than 400 meters. Atypical symptoms may also be considered at the discretion of the investigator, including but not limited to parasthesias, pallor and coolness of the lower peripheral limbs with ambulation.
3. On stable aspirin and statin therapy for at least 6 weeks prior to screening, or have documentation of intolerance. If patients are not on an aspirin or statin, they must have a documented contraindication, e.g. GI distress with aspirin, or statin intolerance or myopathy.
4. Acquisition of evaluable MRI images at baseline to assess the vessel wall morphometry of the superficial femoral artery to determine plaque burden and regions of stenosis.
5. At Screening, and Baseline, vital signs (systolic and diastolic blood pressure and pulse rate) will be assessed in the sitting position after the subject has rested for at least five (5) minutes. An appropriately sized BP cuff should be used for the given subject's body habitus. Vital signs should be within:
   oral body temperature between 35.0-37.5° C.
   systolic blood pressure, 90-170 mm Hg
   diastolic blood pressure, 50-100 mm Hg
   pulse rate, 40-100 bpm The investigational drug, ACZ885 and matching placebo will be prepared by Novartis as lyophilized powder in glass vials and supplied to the clinical sites as open label bulk medication. Please see pharmacy manual for details of preparation. The drug will be delivered at a dose of 150 mg subcutaneously monthly for a treatment period of 12 months.

Subjects will be assigned to one of the following 2 treatments in a ratio of 1:1
Study treatments are defined as:
Monthly doses of 150 mg ACZ885
Monthly doses of placebo to 150 mg ACZ885

REFERENCES

Abbate A, Salloum F N, Veci E. et al (2008) Anakinra, a recombinant human interleukin-1 recptor antagonist, inhibits apoptosis in experimental acute myocardial infarction. Circulation 117:2670-2683

Crossman D C, Morton A C, Gunn J P et al (2008) Investigation of the effect of Interleukin-1 receptor antagonist (IL-1ra) on markers of inflammation in non-ST elevation acute coronary syndromes. (The MRC-ILA-HEART study). Trials; 9:8-21

Hwang M W, Matsumori A, Furukawa Y, et al (2001) Neutralizaqtion of interleukin-1 beta in the acute phase of myocardial infarction promotes the progression of left ventricular remodeling. J Am Coll Cardiol; 38:1546-53

Isoda K and Ohsuzu F (2006) The effect of interleukin-1 receptor antagonist on arteries and cholesterol metabolism. J Atheroscler Thromb; 13:21-30

Isoda K, Shiigai M, Ishigami H et al (2003) Deficiency of interleukin-1 receptor antagonist promotes neointimal formation after injury. Circulation 108:516-8

Kirii H, Niwa T, Yamada Y, et al (2003) Lack of interleukin-1 beta decreases the severity of atherosclerosis in ApoE-deficient mice. Arterioscler Thromb Vasc Biol 23:656-60

Salloum F N, Chau V, Varma A et al (2009) Anakinra in experimental acute myocardial infarction—does dosage or duration of treatment matter? Cardiovasc Drugs Ther 23:129-135

The invention claimed is:

1. A method for treating or alleviating the symptoms of peripheral arterial disease (PAD), comprising administering a subcutaneous dose of about 150 mg to about 300 mg of an IL-1β binding antibody to a subject having symptomatic intermittent claudication and PAD, said subject exhibiting an ankle-brachial index less than 0.9 in at least one leg before treatment, wherein the antibody is administered every month, every two months, or every three months, and wherein the antibody comprises:
   a) a $V_H$ domain comprising the amino acid sequence set forth in SEQ ID NO:1 and a $V_L$ domain comprising the amino acid sequence set forth in SEQ ID NO:2; or
   b) a $V_H$ domain comprising complementarity determining regions (CDRs) 1-3, wherein CDR1 comprises the amino acid sequences set forth as SEQ ID NO:3, CDR2 comprises the amino acid sequences set forth as SEQ ID NO:4, and CDR3 comprises the amino acid sequences set forth as SEQ ID NO:5, and a $V_L$ domain comprising CDRs1-3 wherein CDR1 comprises the amino acid sequences set forth as SEQ ID NO:6, CDR2 comprises the amino acid sequences set forth as SEQ ID NO:7, and CDR3 comprises the amino acid sequences set forth as SEQ ID NO:8.

2. The method according to claim 1, wherein the subject is exhibiting an ankle-brachial index between 0.5 and 0.85 in at least one leg before treatment.

3. The method according to claim 1, wherein the subject has improved vascular structure and function after 3 months of treatment.

4. The method according to claim 1, wherein reduced plaque burden in the peripheral artery walls of said subject is observed after at least 3 months of treatment.

5. The method according to claim 1, wherein a reduced plaque burden compared to before treatment in said subject is determined in the superficial femoral artery after at least 3 months of treatment.

6. The method according to claim 1, wherein a reduced plaque burden compared to before treatment in said subject is determined in the superficial femoral artery after at least 12 months of treatment.

7. The method according to claim 1, wherein said IL-1β binding antibody is administered for a duration of at least one year.

8. The method according to claim 1, wherein the dose of the IL-1β binding antibody is about 150 mg.

9. The method according to claim 1, wherein the dose of the IL-1β binding antibody is about 300 mg.

10. The method according to claim 1, wherein the IL-1β binding antibody is capable of inhibiting the binding of IL-1β to its receptor and has a $K_D$ for binding to IL-1β of about 50 pM or less.

11. The method according to claim 1, wherein said IL-1β binding antibody is canakinumab.

12. The method according to claim 11, wherein canakinumab is administered in a liquid formulation comprising 10-200 mg/ml canakinumab, mannitol, histidine and polysorbate 80, wherein the pH of the formulation is 6.1-6.9.

13. The method according to claim 1, wherein said IL-1β binding antibody is provided for administration to the patient in liquid form in a prefilled syringe or lyophilized form for reconstitution in a prefilled syringe.

14. The method according to claim 1, wherein said patient is concomitantly receiving a statin.

15. The method according to claim 1, wherein said patient is concomitantly receiving a beta-adrenergic blocking drug, an angiotensin-converting enzyme (ACE) inhibitor or an angiotensin II receptor blocker.

* * * * *

```
SEQUENCE LISTING

<160> NUMBER OF SEQ ID NOS: 8

<210> SEQ ID NO 1
<211> LENGTH: 118
<212> TYPE: PRT
<213> ORGANISM: homo sapiens

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30

Gly Met Asn Trp Val Arg Gln Ala Pro Gly Lys Gly Leu Glu Trp Val
        35                  40                  45

Ala Ile Ile Trp Tyr Asp Gly Asp Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95
```

Ala Arg Asp Leu Arg Thr Gly Pro Phe Asp Tyr Trp Gly Gln Gly Thr
            100                 105                 110

Leu Val Thr Val Ser Ser
        115

<210> SEQ ID NO 2
<211> LENGTH: 107
<212> TYPE: PRT
<213> ORGANISM: homo sapiens

<400> SEQUENCE: 2

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Phe
                85                  90                  95

Thr Phe Gly Pro Gly Thr Lys Val Asp Ile Lys
            100                 105

<210> SEQ ID NO 3
<211> LENGTH: 5
<212> TYPE: PRT
<213> ORGANISM: HOMO SAPIENS

<400> SEQUENCE: 3

Val Tyr Gly Met Asn
1               5

<210> SEQ ID NO 4
<211> LENGTH: 17
<212> TYPE: PRT
<213> ORGANISM: HOMO SAPIENS

<400> SEQUENCE: 4

Ile Ile Trp Tyr Asp Gly Asp Asn Gln Tyr Tyr Ala Asp Ser Val Lys
1               5                   10                  15

Gly

<210> SEQ ID NO 5
<211> LENGTH: 6
<212> TYPE: PRT
<213> ORGANISM: HOMO SAPIENS

<400> SEQUENCE: 5

Asp Leu Arg Thr Gly Pro
1               5

<210> SEQ ID NO 6
<211> LENGTH: 11
<212> TYPE: PRT
<213> ORGANISM: HOMO SAPIENS

<400> SEQUENCE: 6

Arg Ala Ser Gln Ser Ile Gly Ser Ser Leu His

```
<210> SEQ ID NO 7
<211> LENGTH: 6
<212> TYPE: PRT
<213> ORGANISM: HOMO SAPIENS

<400> SEQUENCE: 7

Ala Ser Gln Ser Phe Ser
1               5

<210> SEQ ID NO 8
<211> LENGTH: 7
<212> TYPE: PRT
<213> ORGANISM: HOMO SAPIENS

<400> SEQUENCE: 8

His Gln Ser Ser Ser Leu Pro
1               5
```